(12) United States Patent
Leibowitz et al.

(10) Patent No.: US 11,559,292 B2
(45) Date of Patent: Jan. 24, 2023

(54) HANDLE FOR A SURGICAL TOOL

(71) Applicant: Shukla Medical, St. Petersburg, FL (US)

(72) Inventors: Evan G. Leibowitz, Linden, NJ (US); Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 1091 days.

(21) Appl. No.: 16/206,737

(22) Filed: Nov. 30, 2018

(65) Prior Publication Data

US 2020/0155129 A1    May 21, 2020

Related U.S. Application Data

(63) Continuation-in-part of application No. 29/670,724, filed on Nov. 19, 2018, now Pat. No. Des. 914,209.

(51) Int. Cl.
*A61B 17/00* (2006.01)
*B25G 3/18* (2006.01)
*A61B 17/16* (2006.01)

(52) U.S. Cl.
CPC ........... *A61B 17/00* (2013.01); *B25G 3/18* (2013.01); *A61B 17/1604* (2013.01); *A61B 2017/0046* (2013.01); *A61B 2017/00424* (2013.01); *A61B 2017/00473* (2013.01); *A61B 2017/00477* (2013.01)

(58) Field of Classification Search
CPC ........... A61B 2017/00477; A61B 2017/00473; A61B 2017/00424; A61B 2017/0046; A61B 17/1604; A61B 17/00; B25G 3/18
See application file for complete search history.

(56) References Cited

U.S. PATENT DOCUMENTS

| | | |
|---|---|---|
| D791,560 S | 7/2017 | Mitchell |
| 9,956,021 B1 | 5/2018 | Aebi et al. |
| 2004/0171930 A1* | 9/2004 | Grimm ................. A61B 90/39 606/80 |
| 2004/0215058 A1* | 10/2004 | Zirps ..................... A61B 1/018 600/104 |

(Continued)

FOREIGN PATENT DOCUMENTS

WO    2004021867 A2    3/2004

OTHER PUBLICATIONS

Office Action dated Dec. 12, 2020 in European Patent Application No. 19209888.7.

(Continued)

*Primary Examiner* — Andrew M Tecco
*Assistant Examiner* — Nicholas E Igbokwe
(74) *Attorney, Agent, or Firm* — Kim IP Law Group LLC

(57) ABSTRACT

A handle for a surgical tool including a shaft having a proximal end and a distal end with a gripping handle affixed to the proximal end of the shaft. A bushing is attached to the distal end of the shaft, the bushing including a plurality of flexible members circumferentially spaced apart. The handle further includes a sleeve circumscribing the shaft and the bushing. The sleeve is moveable between a first position substantially covering an entirety of the bushing and a second position spaced from a most distal end of the bushing.

16 Claims, 9 Drawing Sheets

(56) References Cited

U.S. PATENT DOCUMENTS

| | | | |
|---|---|---|---|
| 2007/0149850 A1* | 6/2007 | Spivey | A61B 1/00142 600/127 |
| 2013/0160613 A1* | 6/2013 | Brailey | B25B 13/32 81/111 |
| 2014/0243868 A1* | 8/2014 | Parihar | A61B 17/00234 606/1 |

OTHER PUBLICATIONS

Extended European Search Report dated Apr. 24, 2020 in European Patent Application No. 19209888.7.

* cited by examiner

HANDLE FOR A SURGICAL TOOL

CROSS-REFERENCE TO RELATED APPLICATIONS

The present application claims priority under 35 U.S.C. § 120 to U.S. Design patent application No. 29/670,724, filed Nov. 19, 2018 and entitled "Surgical Tool Handle," the disclosure of which is hereby incorporated by reference in its entirety for all purposes.

BACKGROUND OF THE INVENTION

The present disclosure relates generally to a handle for a surgical tool. Specifically, the present disclosure relates to a handle for releasably receiving a surgical tool such as an osteotome and the like.

An osteotome or similar surgical tool is a chisel-like instrument used to cut or divide bone. Conventional handles for surgical tools, such as osteotomes and the like, do not always provide secure gripping of the surgical tool. As such, the tool is not rigidly connected to the handle or has too much play relative to the handle. Consequently, the surgical tool may not operate as precisely and effectively as required.

BRIEF SUMMARY

In accordance with an exemplary embodiment the present disclosure provides a handle for a surgical tool comprising a shaft having a proximal end and a distal end, and a gripping handle affixed to the proximal end of the shaft. A bushing is attached to the distal end of the shaft. The bushing includes a plurality of flexible members circumferentially spaced apart. The tool further comprises a sleeve circumscribing the shaft and the bushing. The sleeve is moveable between a first position substantially covering an entirety of the bushing and a second position spaced from a most distal end of the bushing.

An aspect of the present disclosure is that the handle further comprises a biasing member biasing the sleeve towards the distal end. The biasing member circumscribes a reduced diameter neck portion of the shaft. The reduced diameter neck portion is adjacent the bushing, and the sleeve includes a flange for engaging the bushing. The flange engages a proximally facing surface of the bushing, and a most distal end of the plurality of flexible members is axially spaced from a most distal end of the bushing.

In accordance with an exemplary embodiment the present disclosure provides a handle for a surgical instrument comprising a shaft having a proximal end and a distal end, and a gripping handle attachable to the proximal end of the shaft. A socket extends from the distal end of the shaft. The socket includes a moveable member moveable between a first position defining a first circumference of the socket and a second position defining a second circumference of the socket greater than the first circumference. The handle further comprises a sleeve circumscribing the shaft and the socket. The sleeve is moveable along the axial direction of the shaft.

An aspect of the present disclosure is that the handle further comprises a biasing member biasing the sleeve towards the distal end. The biasing member circumscribes a reduced diameter neck portion of the shaft. The reduced diameter neck portion is adjacent the socket. The sleeve includes a flange for engaging the socket. The flange engages a proximally facing surface of the socket, and a most distal end of the moveable members is axially spaced from a most distal end of the socket.

In accordance with an exemplary embodiment the present disclosure provides a handle for a surgical device comprising a shaft that includes a proximal end having a gripping handle affixed thereto, and a distal end having a blind hole. A circumferential wall defined by the blind hole includes a flexible member moveable between a first position and a second position spaced from the first position. The handle further comprises a sleeve circumscribing the shaft. The sleeve is moveable between a first position substantially circumscribing the flexible member and a second position exposing a portion of the flexible member.

An aspect of the present disclosure is that the handle further comprises a biasing member biasing the sleeve towards the distal end. The shaft includes a reduced diameter neck portion adjacent the circumferential wall defined by the blind hole. The sleeve includes a flange for engaging the circumferential wall defined by the blind hole, and the flange engages a proximally facing surface of the circumferential wall defined by the blind hole. Further, a most distal end of the flexible member is axially spaced from a most distal end of the circumferential wall defined by the blind hole.

In accordance with an exemplary embodiment the present disclosure provides a clutch assembly for grasping a tool comprising a bushing and a sleeve. The bushing includes a plurality of flexible members circumferentially spaced apart. The sleeve circumscribes the bushing and is moveable between a first position substantially covering the bushing and a second position spaced from a distal end of the bushing.

In accordance with an aspect of the present disclosure, the clutch assembly includes a biasing member biasing the sleeve towards the distal end of the bushing, or a biasing member between the sleeve and the bushing for biasing one of the sleeve and the bushing. The sleeve includes a flange for engaging a circumferential wall defined by the bushing and the flange engages a proximally facing surface of the bushing. Further, a most distal end of the flexible member is axially spaced from a most distal end of the bushing.

BRIEF DESCRIPTION OF THE SEVERAL VIEWS OF THE DRAWINGS

The foregoing summary, as well as the following detailed description of the exemplary embodiments of the disclosure, will be better understood when read in conjunction with the appended drawings. For the purpose of illustrating the invention, there are shown in the drawings exemplary embodiments of the disclosure. It should be understood, however, that the invention is not limited to the precise arrangements and instrumentalities shown.

In the drawings.

DETAILED DESCRIPTION

Figure 1:
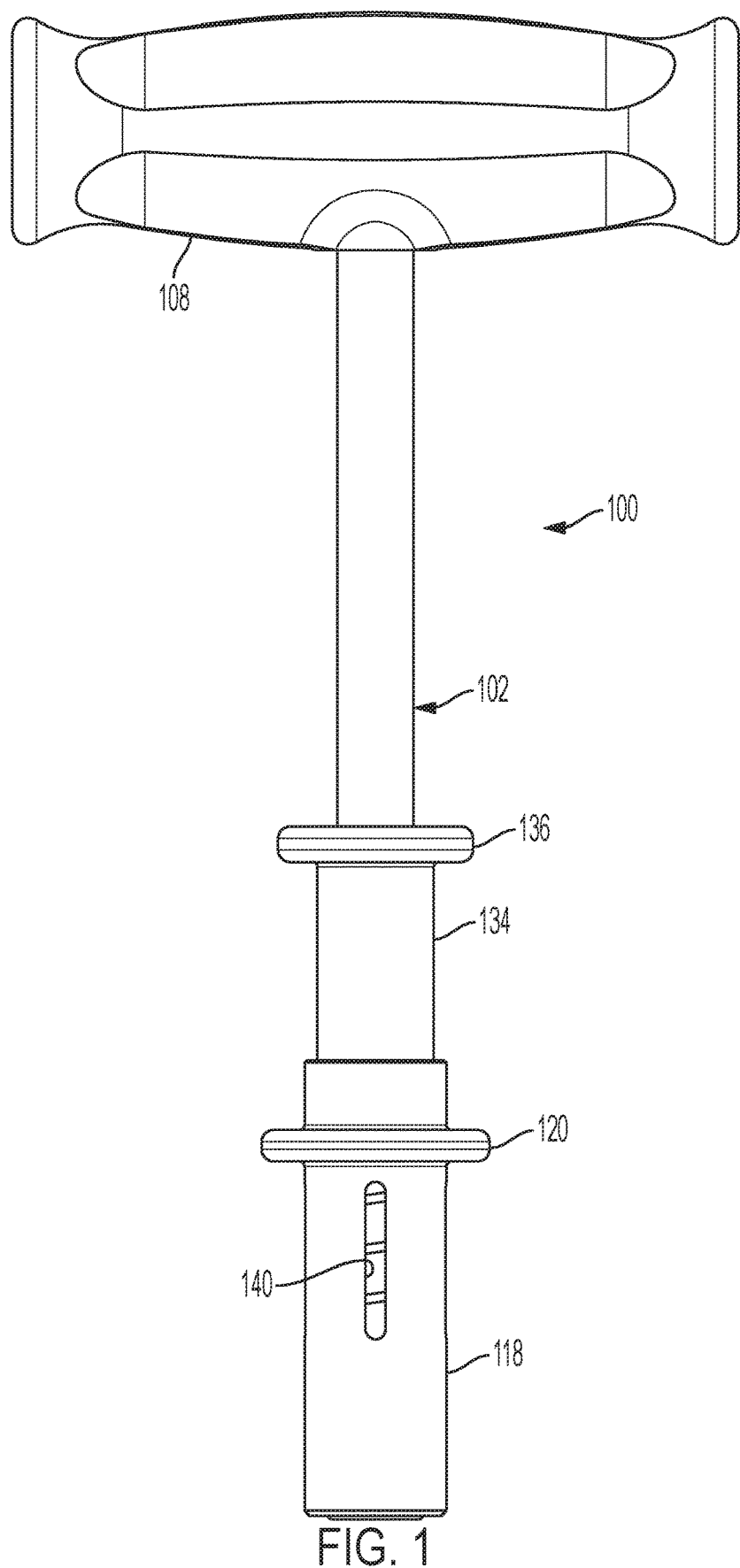
FIG. 1 is an elevational view of a handle for a surgical tool in accordance with an exemplary embodiment of the present disclosure.

Reference will now be made in detail to the various exemplary embodiments illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below, and diagonal are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About," as used herein, when referring to a measurable value such as an amount, a temporal duration, and the like, is meant to encompass variations of ±20%, ±10%, ±5%, ±1%, or ±0.1% from the specified value, as such variations are appropriate.

"Substantially," as used herein, shall mean considerable in extent, largely, but not wholly, that which is specified, or an appropriate variation therefrom as is acceptable within the field of art.

Throughout this disclosure, various aspects of the exemplary embodiments can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages, and characteristics of the exemplary embodiments may be combined in any suitable manner in one or more embodiments. One skilled in the relevant art will recognize, in light of the description herein, that the exemplary embodiments can be practiced without one or more of the specific features or advantages of a particular exemplary embodiment. In other instances, additional features and advantages may be recognized in certain embodiments that may not be present in all exemplary embodiments.

Referring now to the drawings, FIGS. 1 through 8 illustrate an exemplary embodiment of a handle 100 for a surgical tool according to the present disclosure. The handle 100 is configured for releasably holding an unillustrated surgical tool, instrument or device including, but not limited to, an osteotome and the like.

The handle 100 is configured substantially as shown in FIGS. 1 through 8 and includes a shaft 102, a gripping handle 108, a bushing 110 and a sleeve 118. The handle also includes a secondary sleeve 134 attached to and circumscribing the shaft.

The shaft 102 is configured as best shown in FIGS. 1-6 in accordance with an exemplary embodiment of the subject disclosure. The shaft 102 is an elongated cylindrical shaft having a proximal end 104 and a distal end 106. However, the shaft can alternatively be configured as an elongated member having an alternative configuration, such as an annular shaft, or a shaft having a longitudinal cross-section of an oval, an elliptical, or polygonal shape, such as square, hexagonal, octagonal, and the like. The shaft is preferably formed out of a rigid material, such as a metal or composite, suitable for being sterilized.

Figure 4:
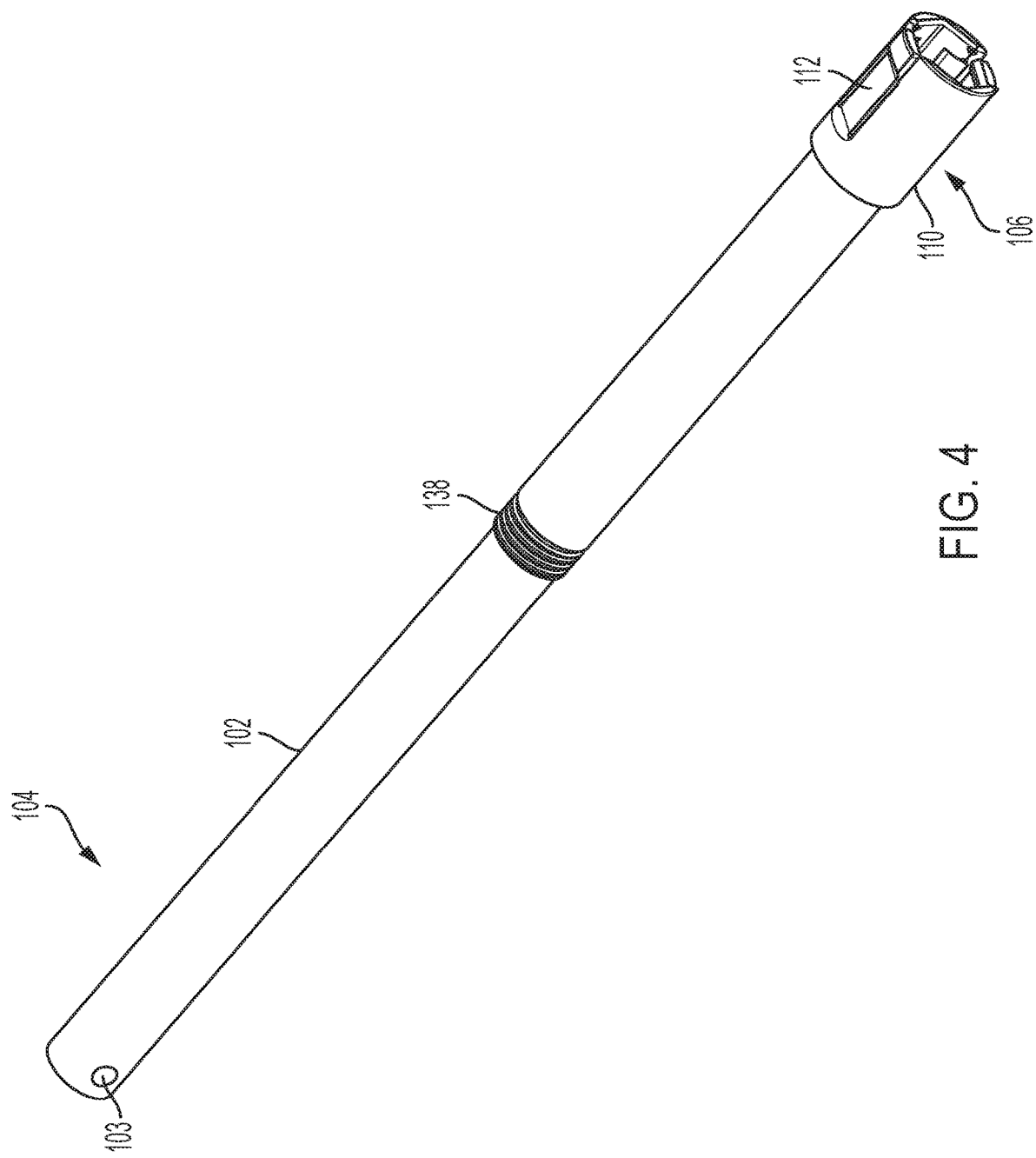
FIG. 4 is a perspective view of a shaft of the handle of FIG. 1.

Referring to FIG. 4, the shaft includes a fastener 138 about its mid-portion. The fastener 138 can be, e.g., threads or a detent, or any other suitable fastener for securely fastening the secondary sleeve 134 thereto (see FIG. 2). The shaft also includes a through hole 103 about its proximal end that extends substantially transverse to a longitudinal axis of the shaft.

Figure 2:
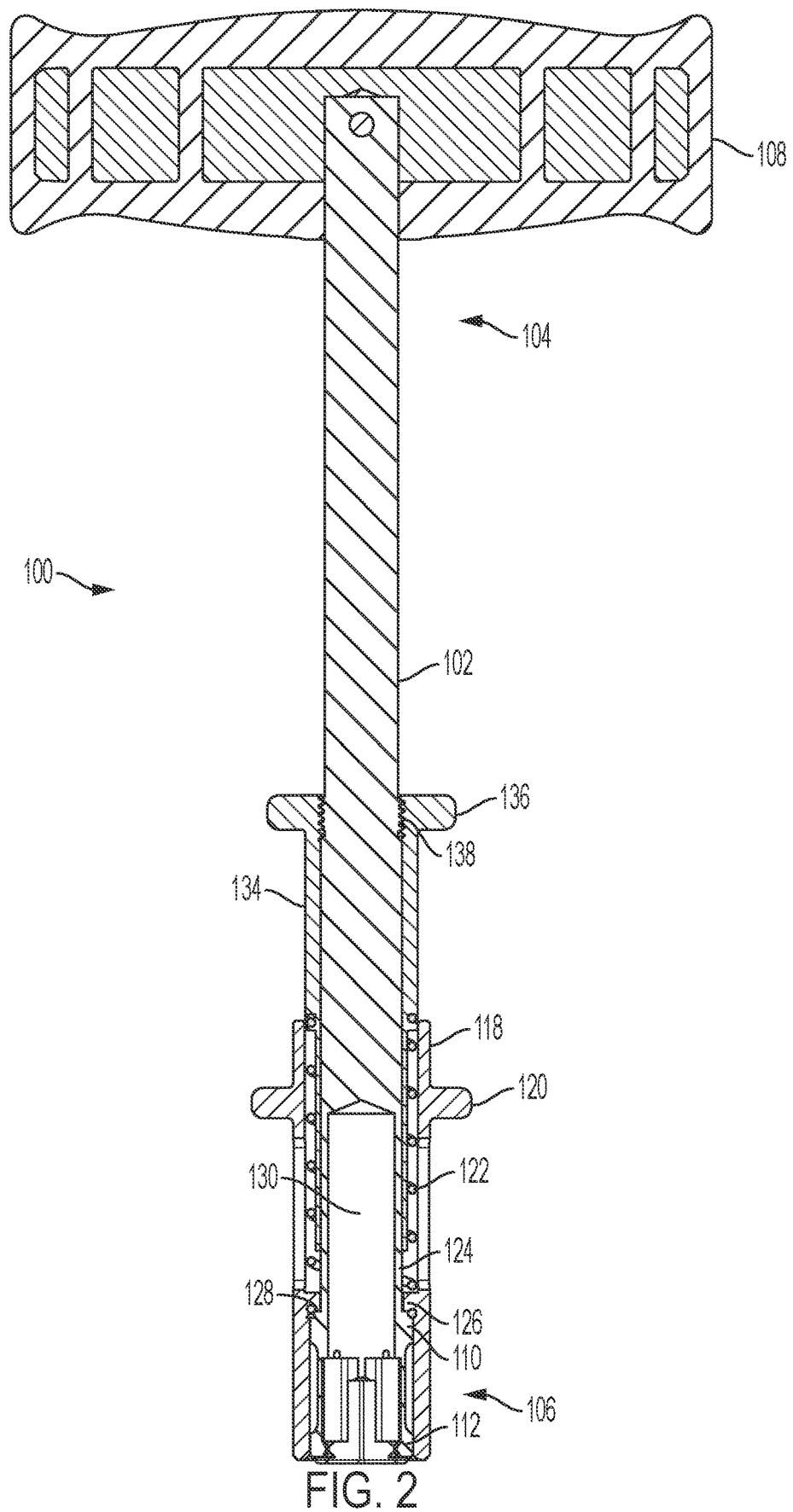
FIG. 2 is an elevational cross-sectional view of the handle of FIG. 1.

Referring to FIG. 2, the distal end of the shaft includes counterbore or blind hole 130 for receiving the surgical tool therein. In the present embodiment, the counter bore extends to about a ¼ of the longitudinal length of the shaft.

In accordance with another embodiment when the shaft is an annular shaft, the counterbore is omitted and a stop feature can be included.

The bushing 110 (also referred to as a socket) is configured as best shown in FIGS. 2-6. The bushing extends from and is attached to the distal end 106 of the shaft. The bushing may be integrally formed with the shaft or it may be affixed thereto by a fastener such as, for example, threading, detent, bonding, friction fit and/or the like. The bushing is configured to have an overall diameter larger than an overall diameter of the shaft adjacent or next to the bushing. In other words, the shaft includes a reduced diameter neck portion 124 adjacent or next to the bushing.

Figure 5:
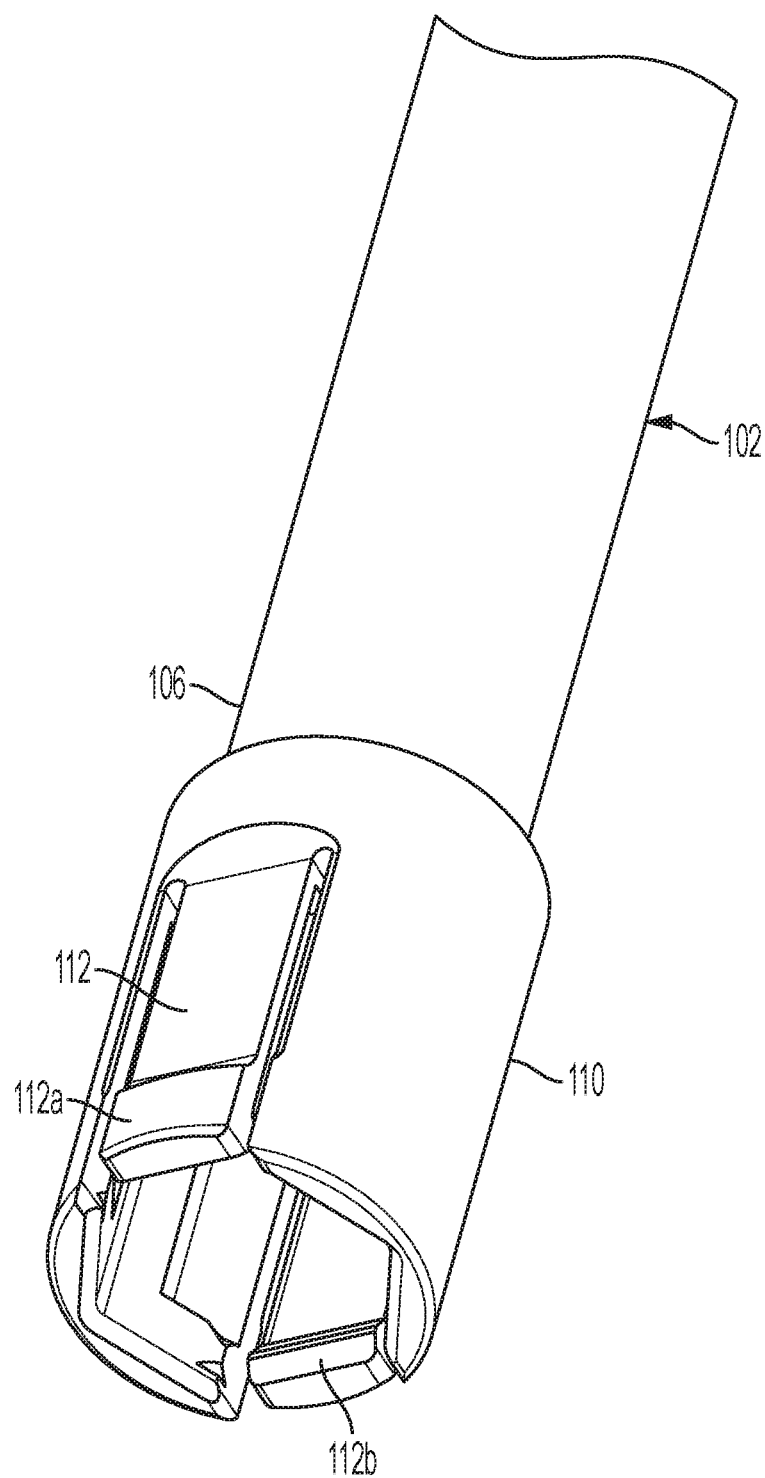
FIG. 5 is an enlarged partial perspective view of a distal end of the shaft of the handle of FIG. 1.
Figure 6:
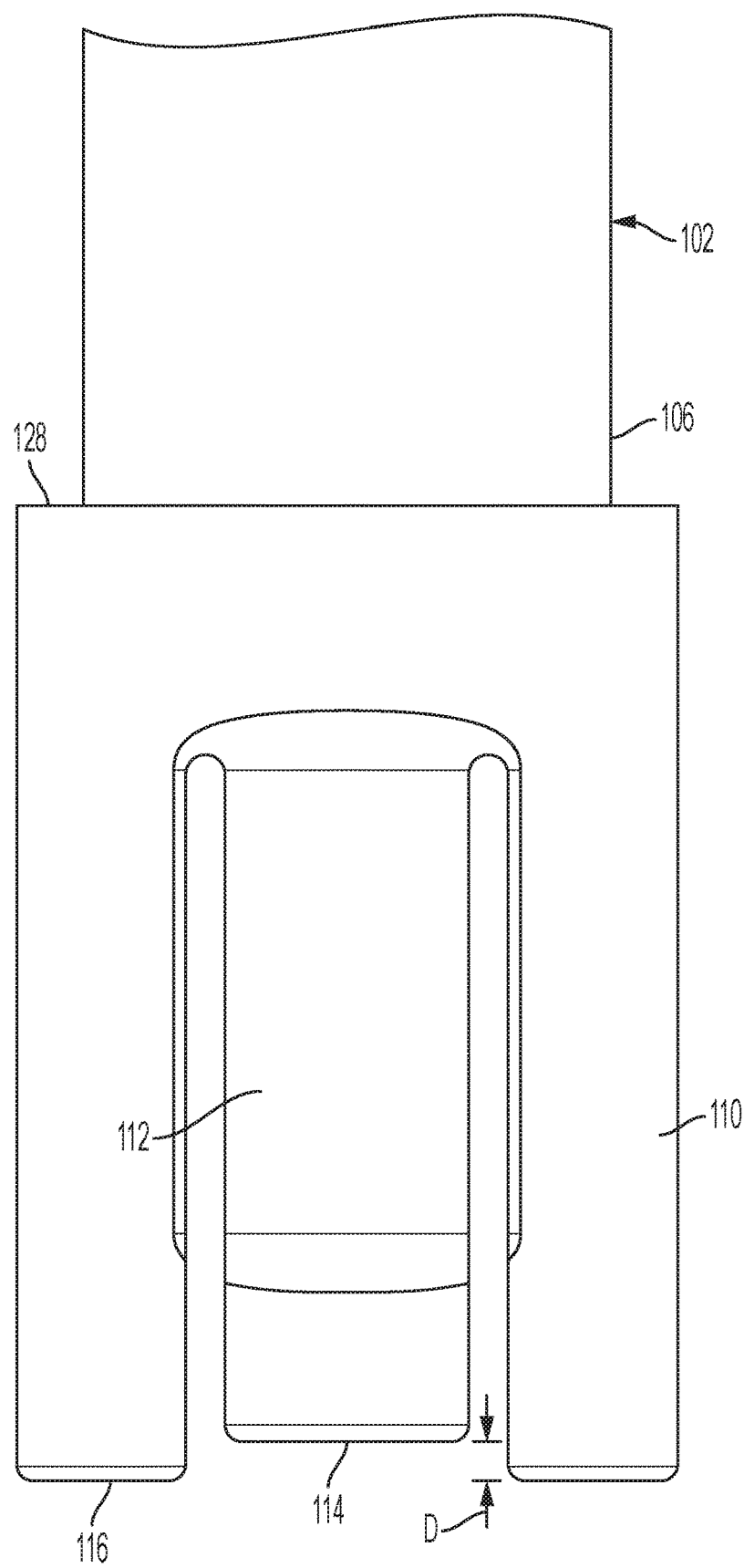
FIG. 6 is an enlarged partial elevational view of a distal end of the shaft of the handle of FIG. 1.

Referring to FIGS. 5 and 6, the bushing 110 includes a plurality of flexible or moveable members 112 circumferentially spaced apart. In the present exemplary embodiment, the bushing includes two flexible members that are diametrically spaced apart. In accordance with an alternative embodiment, the bushing can include more or less the two flexible members such as one, three, four, five, or six.

Each flexible member 112 is formed e.g., as a tab having a distal free end and an attached proximal end. The distal ends of each flexible member 112 include a radially outwardly projecting surface 112a and a radially inwardly projecting surface 112b. The radially outwardly projecting surface 112a is configured to match to overall outer profile of the remainder of the bushing exterior. The radially inwardly projecting surfaces 112b serve to retain and/or grip the surgical tool inserted within the counterbore.

Owing to the free distal end and attached proximal end of each flexible member 112, the flexible members are moveable between a first position defining a first circumference or perimeter of the bushing or socket and a second position defining a second circumference or perimeter of the bushing or socket greater than the first circumference. That is, the second position defines an enlarged opening configured to allow a surgical tool to be received within the counterbore of the shaft and the first position defines a position configured to retain and securely grasp the surgical tool within the handle.

Referring to FIG. 6, a most distal end 114 of each of the plurality of flexible members 112 is axially spaced a distance "D" from a most distal end 116 of the bushing 110. The distance D can be for example 0 to about 0.5 inches, but can alternatively be 0.1, 0.2, 0.3, 0.4, 0.6, 0.7, 0.8, 0.9, 1.0 or more inches depending on the overall size of the handle. The axial spacing of the distal end of the flexible member advantageously allows for greater clearance when moved to an expanded position during a surgical tool insertion, and further serves to guide insertion of the surgical tool into the handle. Alternatively, the flexible member can extend past the most distal end of the bushing so as to extend proud of the bushing's distally facing face.

Referring to FIGS. 1, 2, 7 and 8, the sleeve 118 is configured as shown in accordance with an exemplary embodiment. The sleeve 118 is an annular sleeve that circumscribes the shaft 102, bushing or socket 110, and a biasing member 122 (further discussed below). The sleeve 118 includes a radially outwardly extending flange 120 near its proximal end, and a radially inwardly extending flange 126 near its distal end for engaging the bushing, namely, a proximally facing surface 128 of the bushing. The radially inwardly extending flange 126 is positioned such that the distal end of the sleeve closely matches the distal end of the bushing when the radially inwardly extending flange engages the proximally facing surface 128.

The sleeve portion above the radially inwardly extending flange 126 is sized to have an inside diameter greater than the outside diameter of the shaft so as to form an annular pocket where the biasing member 122 is to be positioned. This inside diameter portion is also sized to closely match the outside diameter of the secondary sleeve 134 such that the sleeve 118 can slide or move relative to the secondary sleeve. The sleeve portion below the radially inwardly extending flange 126 is sized to have an inside diameter that closely matches the overall outside diameter of the bushing, as best shown in FIG. 2.

The flange 120 is configured to have a size sufficient to allow the fingers of a user to easily grasp the sleeve and to apply a pulling force. The radially inwardly extending flange 126 is sized to closely match the outside diameter of the shaft adjacent and above the bushing.

Figure 7:
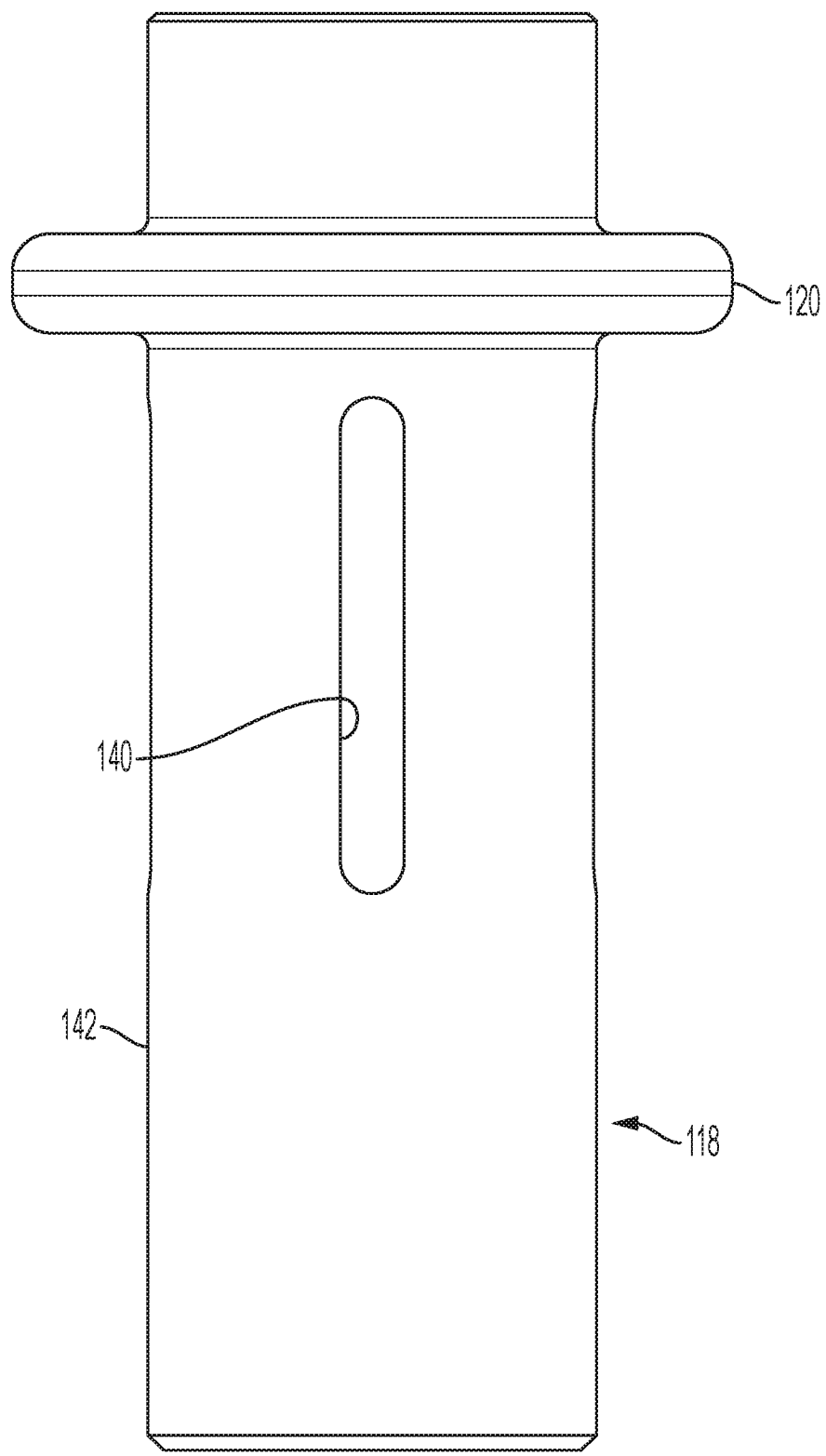
FIG. 7 is an enlarged elevational view of a sleeve of the handle of FIG. 1.
Figure 8:
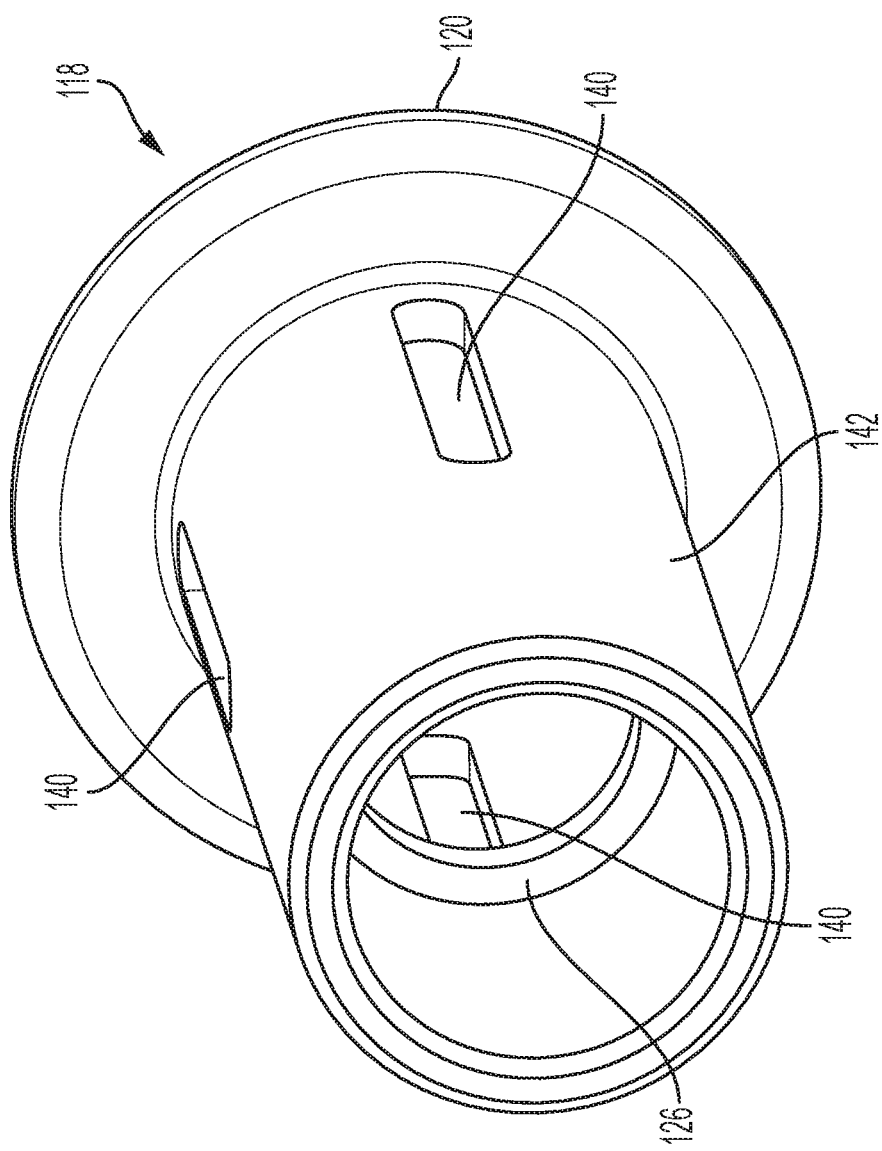
FIG. 8 is a bottom perspective view of the sleeve of FIG. 7.

Referring to FIGS. 7 and 8, the sleeve 118 can also include one or more openings or slots 140 formed along its sidewall 142. The openings 140 permit ingress of cleaning and/or sterilizing agents to the interior of the sleeve such that the elements of the handle 100 located inside of the sleeve may be cleaned and/or sterilized before and after a surgical procedure.

The sleeve 118 moveable along the axial direction of the shaft between a first position and a second position. In the first position (FIG. 1), the sleeve covers substantially an entirety of the bushing and circumscribes the flexible members 112. In the second position (FIG. 1A), the sleeve is spaced from a most distal end of the bushing, thereby exposing a portion or entirety of the flexible member 112 such that the flexible members can move radially outwardly to allow access and receipt of a surgical tool within the handle.

The secondary sleeve 134 is fixed in position to the shaft 102 by the fastener 138. In the present exemplary embodiment, the secondary sleeve includes threads for cooperatively engaging threads i.e., fastener 138, on the shaft. The secondary sleeve includes a radially outwardly extending flange 136.

The handle also includes the biasing member 122 which is positioned on the shaft to bias the sleeve 118 towards the distal end of the shaft 102. The biasing member 122 can be any biasing member suitable for its intended purpose, for example a compression spring, leaf spring, elastomer and the like. The biasing member biases the sleeve towards the distal end. The biasing member also circumscribes the reduced diameter neck of the shaft.

In the present exemplary embodiment, the biasing member is positioned between the shaft and the sleeve 118 and configured as a compression spring that circumscribes the shaft 102 above the bushing. A proximal end of the biasing member engages the secondary sleeve 134 and the distal end of the biasing member engages the radially inwardly extending flange 126 so as to provide a biasing fore to bias the sleeve 118 towards the first position (FIG. 1).

Figure 1A:
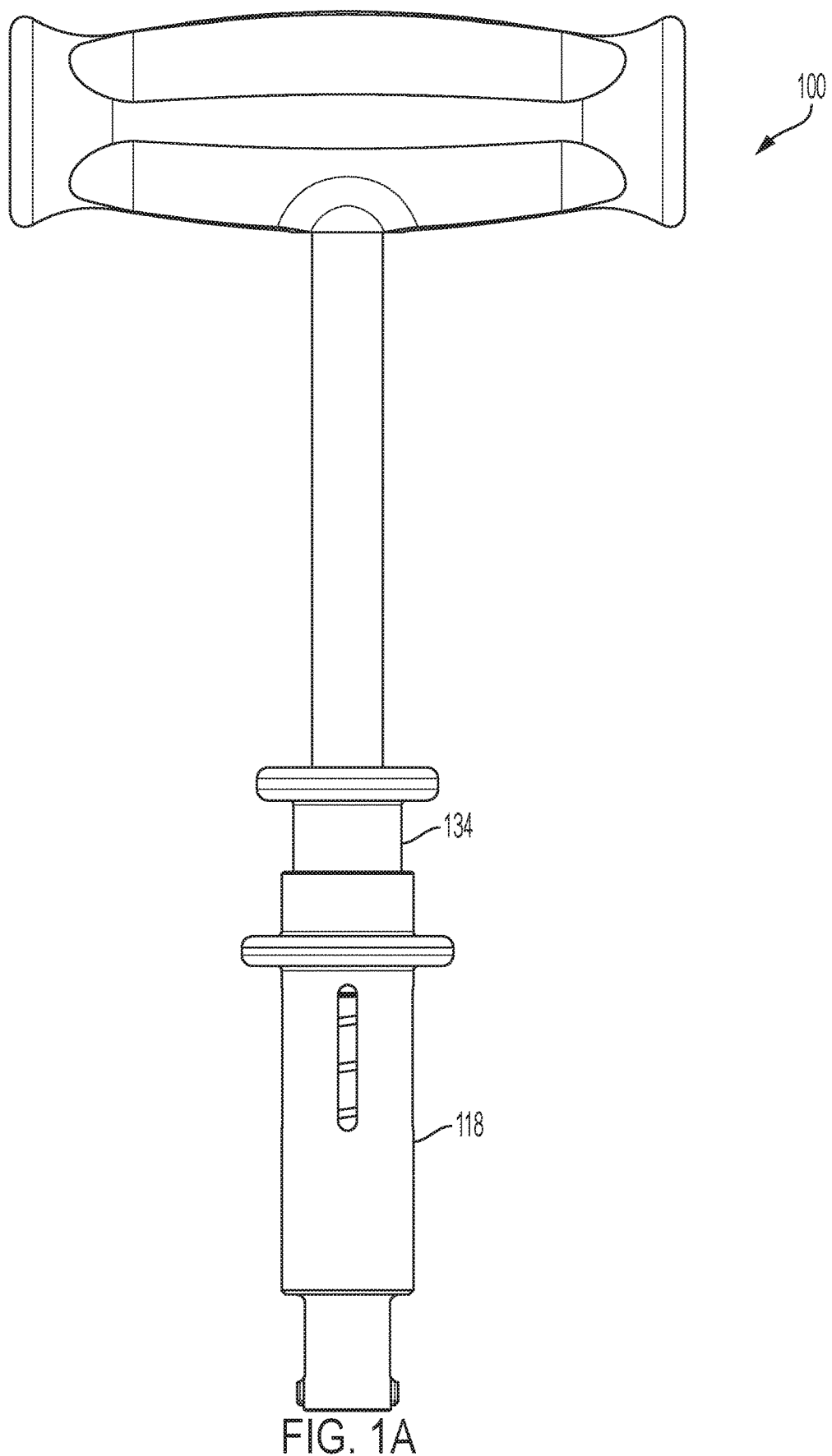
FIG. 1A is an elevational view of the handle of FIG. 1 with a sleeve in a retracted position.
Figure 3:
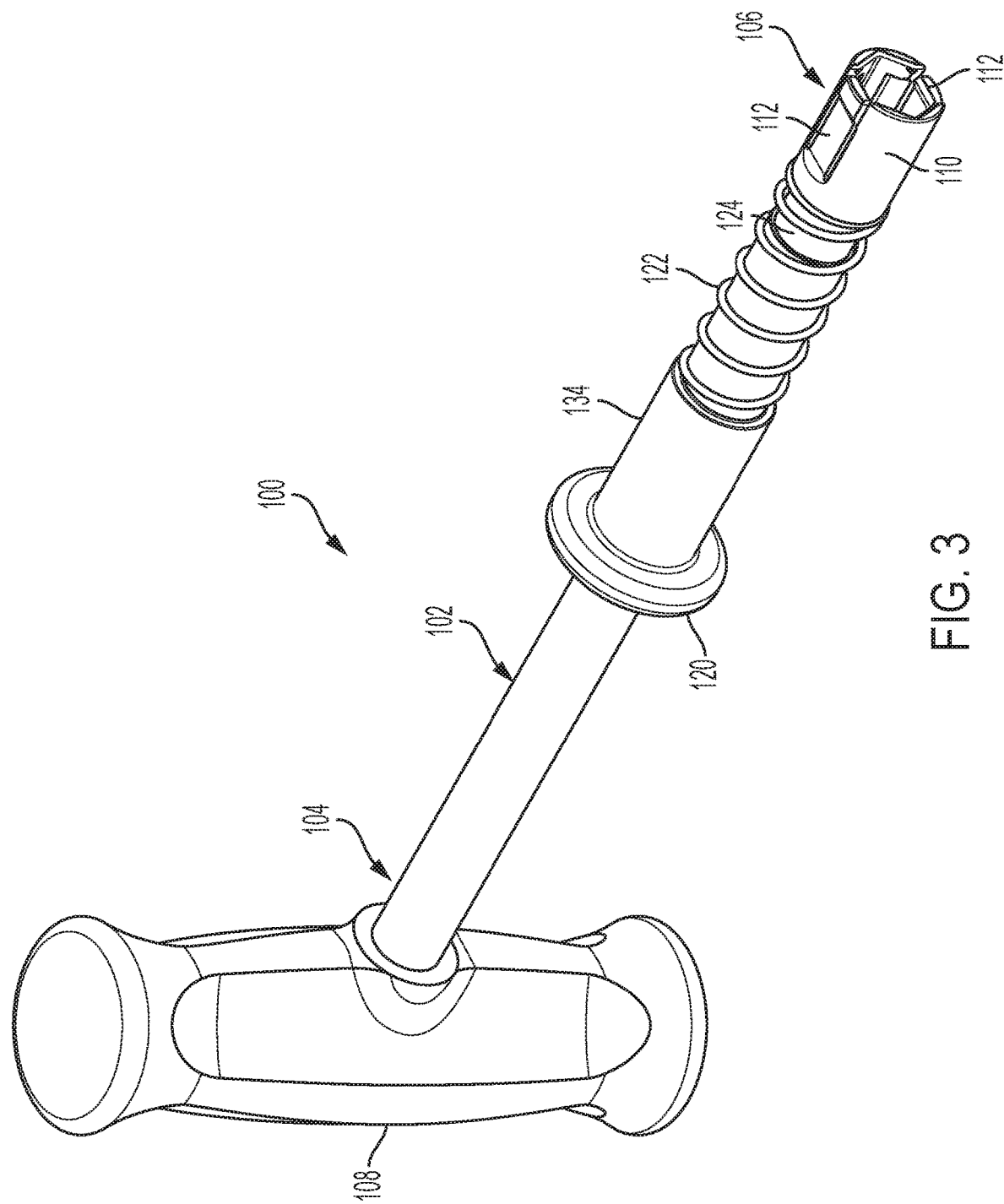
FIG. 3 is a perspective view of the handle of FIG. 1 with certain elements omitted for clarity of illustration.

The gripping handle 108 is configured as best shown in FIGS. 1-3 and may be fabricated from substantially rigid to rigid materials, as well as non-rigid materials e.g., thermoplastics, elastomers, rubber, neoprene, and the like. The gripping handle 108 can be molded directly onto the proximal end 104 of the shaft 102 or be attachable e.g., mechanically attached by way of a fastener, or bonded thereto. In general, the gripping handle is configured to ergonomically receive a user's grip.

Alternatively expressed, the exemplary embodiment of the handle for a surgical device includes a shaft having a proximal end having a gripping handle affixed thereto and a distal end having a blind hole. A circumferential wall defined by the blind hole (referred to above as the bushing) includes the flexible members 112 moveable between a first position and a second position spaced from the first position. The blind hole is configured as discussed above for the bushing.

Additionally, the bushing 110 and sleeve 118 collectively form a clutch assembly for grasping a tool. As discussed above, the bushing includes a plurality of flexible members 112 circumferentially spaced apart. The sleeve circumscribes the bushing and is moveable between a first position substantially covering the bushing and a second position spaced from a distal end of the bushing or spaced from the first position. The sleeve is sized to closely match the overall outside diameter of the bushing so as to fix the flexible members in position when substantially covering the bushing.

The clutch assembly can also include a biasing member, such as biasing member 122 discussed above, biasing the sleeve towards the distal end of the bushing, or a biasing member between the sleeve and the bushing for biasing one of the sleeve and the bushing. The sleeve includes a flange for engaging a circumferential wall defined by the bushing. The sleeve is a radially inwardly extending flange, such as flange 126 discussed above. The flange is configured to engage a proximally facing surface of the bushing. Further, a most distal end of the flexible member is axially spaced from a most distal end of the bushing, as similarly discussed above.

In operation, a user engages the flange 136 with his or her thumb and the flange 120 of the sleeve 118 with one or more of his or her fingers and pulls the sleeve towards the flange 136, thereby overcoming the bias of the biasing member 122 and moving sleeve 118 to a position from a distal end of the bushing or socket or blind hole 110 and exposing at least a portion of the moveable or flexible members 112. The moveable or flexible members 112, in turn, can be moved from a first position to a second position spaced from the first position upon interference insertion of the surgical tool into the counterbore. In other words, the moveable or flexible members 112 are moveable between a first position defining a first circumference of the socket and a second position defining a second circumference of the socket greater than the first circumference such that the surgical tool can be inserted into the counterbore.

Following insertion of a surgical tool, device or instrument into the socket/bushing/blind hole 110 at the distal end 106 of the shaft 102, the user permits the sleeve 118 to move away from the secondary sleeve 134 under the biasing force of the biasing member 122. In so doing, the distal end of the sleeve 118 circumscribes the flexible or moveable members 112 and urges the flexible or moveable members into firm, gripping contact with the surgical tool and locks the socket/bushing/blind hole in the first position.

It will be appreciated by those skilled in the art that changes could be made to the exemplary embodiments described above without departing from the broad inventive concept thereof. It is to be understood, therefore, that the present invention is not limited to the particular exemplary embodiments disclosed, but it is intended to cover modifications within the spirit and scope of the present invention as defined by the claims.

What is claimed is:

1. A handle for a surgical tool comprising:
   a shaft having a proximal end and a distal end;
   a gripping handle affixed to the proximal end of the shaft;
   a bushing attached to the distal end of the shaft, the bushing including a plurality of flexible members circumferentially spaced apart; and
   a sleeve circumscribing the shaft and the bushing, wherein the sleeve is moveable between a first position substantially covering an entirety of the bushing and a second position spaced from a most distal end of the bushing, and wherein the sleeve includes a flange that engages a proximally facing surface of the bushing.

2. The handle of claim 1, further comprising a biasing member biasing the sleeve towards the distal end.

3. The handle of claim 2, wherein the biasing member circumscribes a reduced diameter neck portion of the shaft.

4. The handle of claim 1, wherein the shaft includes a reduced diameter neck portion adjacent, the bushing.

5. The handle of claim 1, wherein a most distal end of the plurality of flexible members is axially spaced from a most distal end of the bushing.

6. A handle for a surgical instrument comprising:
   a shaft having a proximal end and a distal end;
   a gripping handle attachable to the proximal end of the shaft;
   a socket extending from the distal end of the shaft, the socket including a moveable member moveable between a first position defining a first circumference of the socket and a second position defining a second circumference of the socket greater than the first circumference; and
   a sleeve circumscribing the shaft and the socket, wherein the sleeve is moveable along the axial direction of the shaft.

7. The handle of claim 6, further comprising a biasing member biasing the sleeve towards the distal end.

8. The handle of claim 7, wherein the biasing member circumscribes a reduced diameter neck portion of the shaft.

9. The handle of claim 6, wherein the shaft includes a reduced diameter neck portion adjacent the socket.

10. The handle of claim 6, wherein the sleeve includes a flange for engaging the socket.

11. The handle of claim 10, wherein the flange engages a proximally facing surface of the socket.

12. The handle of claim 6, wherein a most distal end of the moveable members is axially spaced from a most distal end of the socket.

13. A clutch assembly for grasping a tool comprising:
    a bushing having a plurality of flexible members circumferentially spaced apart; and
    a sleeve circumscribing the bushing and moveable between a first position substantially covering the bushing and a second position spaced from a distal end of the bushing, wherein the sleeve includes a flange that engages a proximally facing surface of the bushing.

14. The clutch assembly of claim 13, further comprising a biasing member biasing the sleeve towards the distal end of the bushing.

15. The clutch assembly of claim 13, further comprising a biasing member between the sleeve and the bushing for biasing one of the sleeve and the bushing.

16. The clutch assembly of claim 13, wherein a most distal end of the flexible member is axially spaced from a most distal end of the bushing.

* * * * *